United States Patent [19]

Sturgill et al.

[11] Patent Number: 5,188,112
[45] Date of Patent: Feb. 23, 1993

[54] ULTRASONIC DOPPLER IMAGING SYSTEMS WITH IMPROVED FLOW SENSITIVITY

[75] Inventors: Michael R. Sturgill, Phoenix; Bradley K. Herres, deceased late of Scottsdale, Muriel Herres, legal representative; Paul M. Jaeger, Mesa, all of Ariz.

[73] Assignee: Acoustic Imaging Technologies Corporation, Phoenix, Ariz.

[21] Appl. No.: 614,258

[22] Filed: Nov. 16, 1990

Related U.S. Application Data

[63] Continuation-in-part of Ser. No. 527,565, May 23, 1990, abandoned, which is a continuation-in-part of Ser. No. 441,861, Nov. 27, 1989, abandoned.

[51] Int. Cl.$^5$ .............................................. A61B 8/06
[52] U.S. Cl. ............................ 128/661.09; 73/861.25
[58] Field of Search ..................... 128/661.08–661.1; 73/861.25

[56] References Cited

U.S. PATENT DOCUMENTS

| Re. 32,323 | 1/1987 | Bom | 128/660.1 |
|---|---|---|---|
| 4,324,258 | 4/1982 | Huebscher et al. | 128/663 |
| 4,409,982 | 10/1983 | Plesset et al. | 128/660.1 |
| 4,509,525 | 4/1985 | Seo | 128/660.05 |
| 4,583,552 | 4/1986 | Iinama | 128/660.05 |
| 4,622,977 | 11/1986 | Namekawa et al. | 128/661.09 |
| 4,641,668 | 2/1987 | Namekawa | 128/661.09 |
| 4,790,323 | 12/1988 | Leavitt et al. | 128/661.09 |
| 4,803,990 | 2/1989 | Bonnefous et al. | 128/661.09 |
| 4,809,703 | 3/1989 | Ishikawa et al. | 128/661.09 |
| 4,817,619 | 4/1989 | Sugiyama et al. | 128/661.09 |
| 4,830,016 | 5/1989 | Tamano et al. | 128/661.09 |
| 4,848,355 | 7/1989 | Nakamura et al. | 128/661.07 |
| 4,883,060 | 11/1989 | Pesque et al. | 128/660.01 |
| 4,888,694 | 12/1989 | Chesarek | 128/660.01 X |

FOREIGN PATENT DOCUMENTS

0197854  3/1986  European Pat. Off.

OTHER PUBLICATIONS

Fehr, R., et al., "Pulsed MTS Doppler Velocimeter...." Biomedizinische Technik, vol. 21 (Supplement), pp. 289–290, Jun. 1976.
Brandestini, "Topoflow–A Digital Full Range Doppler Velocity Meter," *IEEE Transactions on Sonics and Ultrasonics*, vol. SU-25, No. 5, Sep. 1978.
"Circuit Theory and Design," G. S. Moschytz and J. Neirynck (Editors), in Proceedings of the 1978 European Conference on Circuit Theory and Design, title page, and pp. 528–532.
European Search Report.

*Primary Examiner*—Francis Jaworski
*Attorney, Agent, or Firm*—Christie, Parker & Hale

[57] ABSTRACT

An ultrasonic blood flow measuring and imaging system comprises a transmit-receive transducer for transmitting ultrasonic waves toward and into the human body and for receiving reflected echo signals which are then processed for use in a Doppler blood flow imaging and display system. Multiple ultrasonic pulse beams are transmitted into the body at each of a number of angles in an area under diagnosis. For each angle, a plurality of reflected echo signals are received during successive predetermined time intervals. Each received echo signal has a stationary component reflected from essentially stationary tissue and a Doppler component reflected from areas where movement is sensed, such as blood flow. The reflected echo signals are processed in an MTI filter subtracting a stationary component from the received echo signals to thereby extract a Doppler signal representative of a Doppler component of the received echo signals. The Doppler component is then processed in an MTI filter equalizer having a frequency response which is the inverse of the MTI filter, for producing an output having an essentially flat frequency response over the range of frequencies being measured. The output is used to produce color flow imaging of the blood flow in the area under diagnosis.

40 Claims, 7 Drawing Sheets

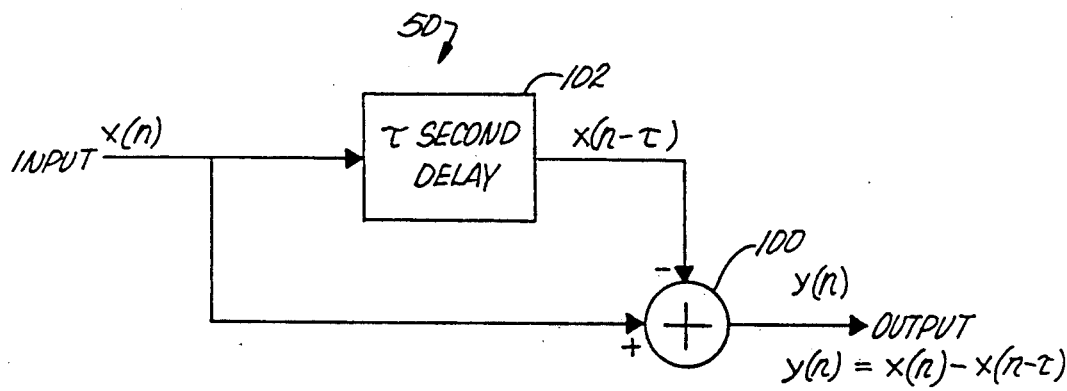
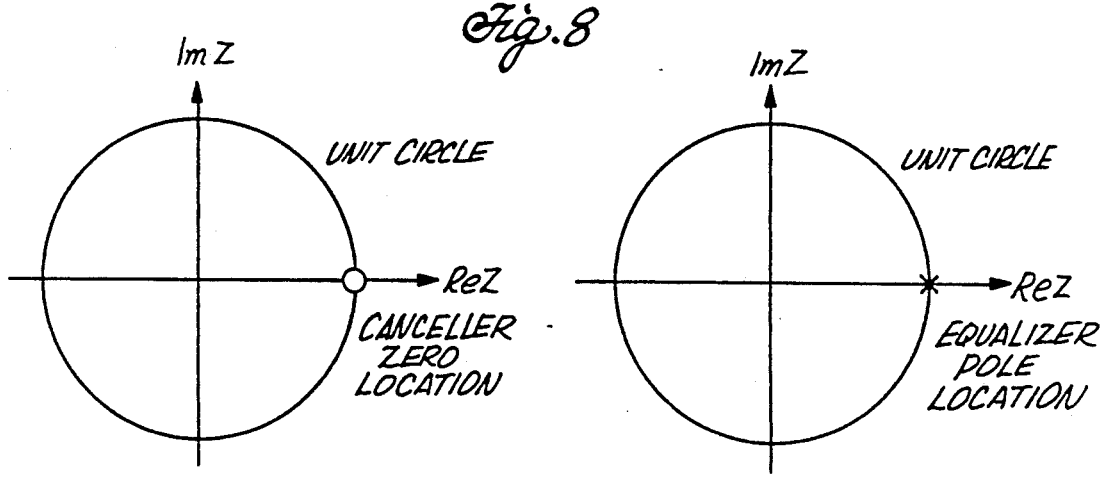

ULTRASONIC DOPPLER IMAGING SYSTEMS WITH IMPROVED FLOW SENSITIVITY

CROSS-REFERENCE

This is a continuation-in-part of application Ser. No. 07/527,565, filed May 23, 1990, entitled "Ultrasonic Doppler Imaging With Analog Feedback Signal Canceller," and now abandoned which is a continuation-in-part of application Ser. No. 07/441,861, filed Nov. 27, 1989 and now abandoned, both applications being incorporated herein by this reference.

FIELD OF THE INVENTION

This invention relates to ultrasonic diagnosis techniques, and more particularly, to ultrasonic Doppler blood flow imaging and display systems. The invention is particularly directed to techniques for improving the dynamic slow flow sensitivity of an ultrasonic color flow imaging system.

BACKGROUND OF THE INVENTION

Various techniques have been used in the past to achieve noninvasive imaging of blood flow using ultrasound. Recent developments in Doppler echocardiography are an example. Although the present invention is applicable to other uses, it will be described below in connection with its applicability to Doppler ultrasound blood flow imaging.

A typical ultrasound blood flow imaging system includes an ultrasonic transmit-receive transducer for transmitting ultrasonic pulses into a region of the body under diagnosis and for receiving echo signals of the transmitted ultrasound waves reflected due to blood flow in the area being scanned. One type of transducer is in the form of a probe containing a curved linear array of piezoelectric elements that insonify a sector shaped area of the body. A typical diagnosis with ultrasound includes scanning the patient with the ultrasound probe to measure blood flow in an artery, a vein, or in the heart. A signal processing system processes the received echo signals for measuring the Doppler shift frequency of the echo signals to thereby calculate the velocity of the blood flow, and the result of the velocity distribution measurement is displayed as a Doppler blood flow image. Techniques have been conventionally used for displaying the Doppler shift as a black and white image displaying velocity (B-mode gray scale display of echo amplitudes); in more recent years, color imaging techniques have been developed for displaying the two dimensional velocity distribution of blood flow in the area under diagnosis.

In order to estimate the Doppler shifts of the echoes received from the blood cells, an ultrasonic imaging system commonly transmits several (e.g. 4-16) pulses at one angle in the region under diagnosis and then detects the variations in the phase of the echoes from pulse to pulse.

Echo signal components Doppler-shifted by the blood flow are extracted from the Doppler signal components carrying the information of the internal moving part of the body. Echo signal components reflected from stationary targets, such as stationary tissue, are removed. These stationary signals are referred to as "clutter." They must be removed since their relative amplitude is typically orders of magnitude greater than the Doppler-shifted signals contained in the same data.

A stationary cancelling filter (also called a moving target indication filter or MTI) is used to eliminate clutter signals caused by stationary objects. In a typical MTI filter, echo signals from consecutive sound receptions are subtracted. Since the echoes from blood flow are superimposed on a much stronger tissue echo, the subtraction steps can, on the average, eliminate the signal due to stationary objects and extract the Doppler component representing blood flow. The MTI filter output is then processed by a velocity estimator to extract the Doppler frequency information, which is converted to velocity data signals suitable for display in color or on a B-mode gray scale display of echo amplitudes.

A principal object in the design and development of a Doppler color flow imaging system is to improve flow image quality, including slow flow sensitivity. These objectives can be achieved by signal processing techniques that result in higher Doppler signal-to-clutter ratios. It is also important to provide such improvements without adversely affecting system costs or image frame rates.

One limitation in the slow flow sensitivity of prior art systems arises from the use of the MTI filter, which has a frequency response which is not flat in the frequency range which includes the Doppler frequency signals representing blood flow. As a result of this frequency response characteristic, the MTI output signal contains a spectral bias which, when processed by the velocity estimator, produces errors in the blood flow estimate.

SUMMARY OF THE INVENTION

One embodiment of the present invention provides an analog feedback stationary bias signal canceller for ultrasound flow imaging having improved Doppler signal-to-noise ratios. Briefly, this embodiment of the invention includes an ultrasonic wave transmitting and receiving device for sequentially transmitting ultrasonic pulses toward and into a living body at a selected angle over a predetermined time interval and for receiving a corresponding series of reflected echo signals. In each flow measuring sequence, a series of ultrasound signals in the form of pulse echo sequences, each representing an acoustic line, are transmitted toward and received from a selected location under diagnosis at a selected angle over a predetermined time interval. Each received echo signal has a stationary component representative of reflection from essentially stationary tissue and a Doppler component representative of reflection from a faster moving part of the body such as blood flow. The echo signals received during successive predetermined time intervals are processed by signal processing means which include (i) means for subtracting a stationary bias component from the received echo signals to thereby extract from the echo signals a Doppler signal representative of a Doppler component of the received echo signals, and (ii) means for thereafter amplifying the Doppler signal to produce a succession of output signals representative of the amplified Doppler components of the reflected echo signals. The extracted and amplified Doppler output signals are then processed to generate Doppler flow image data signals for use in imaging the moving part of the body under diagnosis.

In a preferred form of the invention, the reflected echo signals are processed in an analog feedback stationary bias signal canceller having bias signal acquisition and Doppler signal acquisition modes. During each flow measuring sequence, the signals from one ultrasound line are converted to digital form and stored in a line buffer. The system then switches to the Doppler acquisition mode, and on each of the succeeding pulses during the same flow measuring sequence, the stored line sample, representing signal bias, is recalled from the line buffer, converted to analog form, and subtracted from the succeeding reflected echo signals. The difference is then amplified, converted to digital form, and processed by an MTI filter and velocity estimator to thereby produce Doppler flow image data for use in imaging, including color imaging, of blood flow (velocity) in the area under diagnosis.

As one advantage of this invention, the system produces a higher ratio of Doppler signal-to-quantization noise and permits the use of less expensive analog-to-digital converters, with only a small decrease in image frame rate.

Another embodiment of this invention provides a means for equalizing the response characteristics of an MTI filter for improved slow flow sensitivity in an ultrasound flow imaging system. In a preferred form of this invention, the reflected echo signals are processed in an MTI filter equalizer. During each flow measuring sequence, the signals from one ultrasound line are first digitized with an analog-to-digital converter and stored in a memory buffer. The signal is then processed by the MTI filter and the output signal from the MTI filter input to an MTI filter equalization network having means for producing a frequency response which is the inverse of the MTI filter. The resulting output from the equalization network has an essentially flat gain over the frequency range at which flow is being measured. The equalizer output at lower frequencies (very low and baseband frequencies) is essentially zero. The output from the equalizer is processed by the Doppler flow imaging system, including velocity estimation and color imaging, to produce image data representative of the blood flow in the area under diagnosis. The equalizer enhances accuracy of flow measurements at low flow rates by substantially reducing the spectral bias introduced by the MTI filter, and increasing the gain at the frequencies of interest.

One advantage of this invention is that it produces a higher signal-to-quantization noise ratio of the slowly moving blood flows and allows a substantially unbiased Doppler spectral estimate to be made for all flow velocities of interest. The equalization network produces no decrease in image frame rate with only a slight but tolerable increase in processing complexity.

These and other aspects of the invention will be more fully understood by referring to the following detailed description and the accompanying drawings.

BRIEF DESCRIPTION OF THE DRAWINGS

FIG. 6 is a functional block diagram showing how an MTI filter is implemented. The variables are shown in the form of difference equations.

FIG. 8 shows pole zero diagrams of the MTI filter and the filter equalizer. The circle indicates the location of the zero in the MTI filter and the "x" indicates the theoretical pole location of the filter equalization network as described in the detailed description to follow.

DETAILED DESCRIPTION

Figure 1:
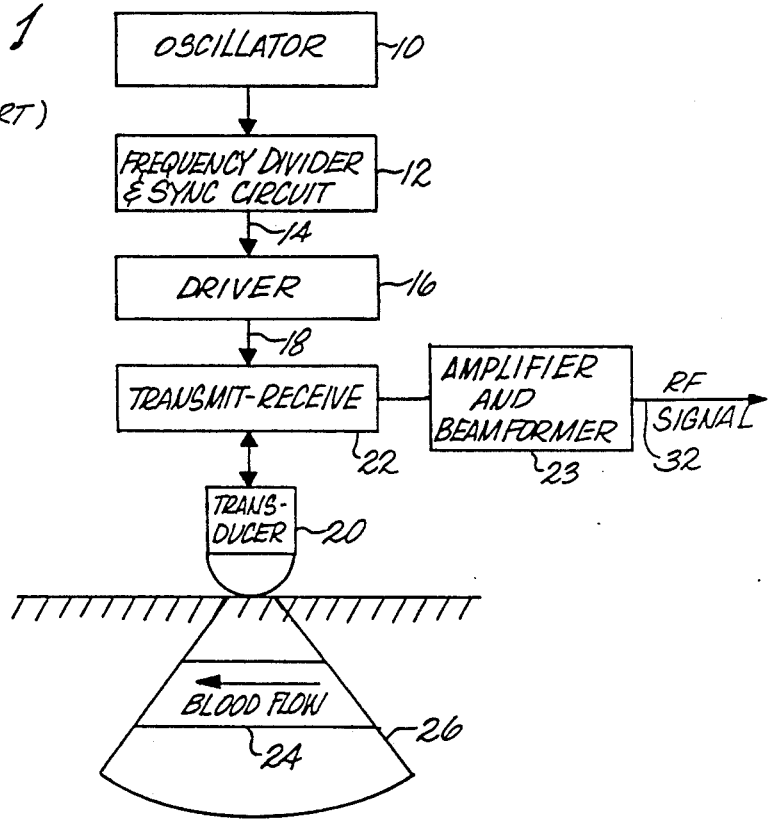
FIG. 1 is a schematic functional block diagram illustrating components of a blood flow measuring system for producing input signals to the systems shown in FIGS. 2, 4, 5 or 13.
Figure 3:
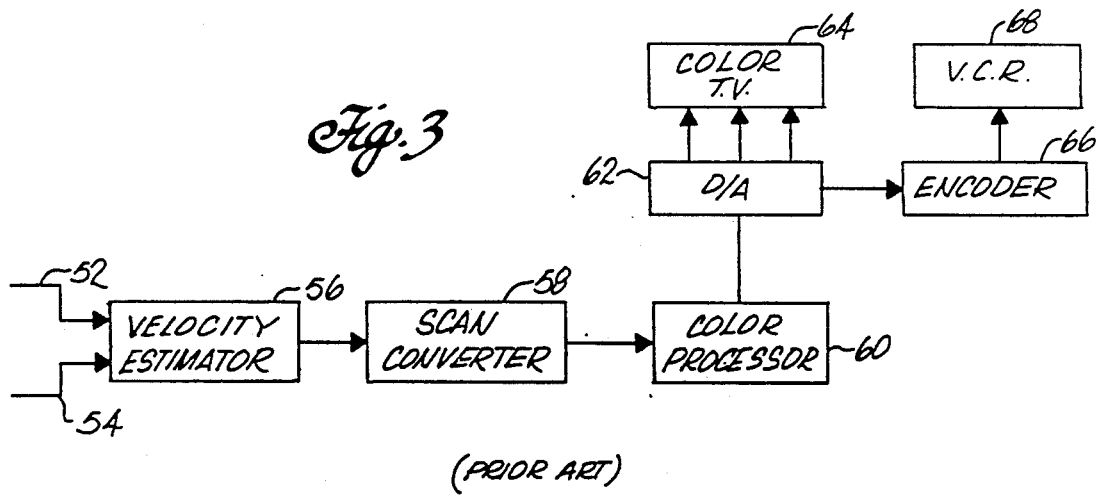
FIG. 3 is a functional block diagram illustrating a velocity estimator and display subsystem for conventional processing of the information produced by the systems shown in FIGS. 2, 4, 5 or 13.
Figure 2:
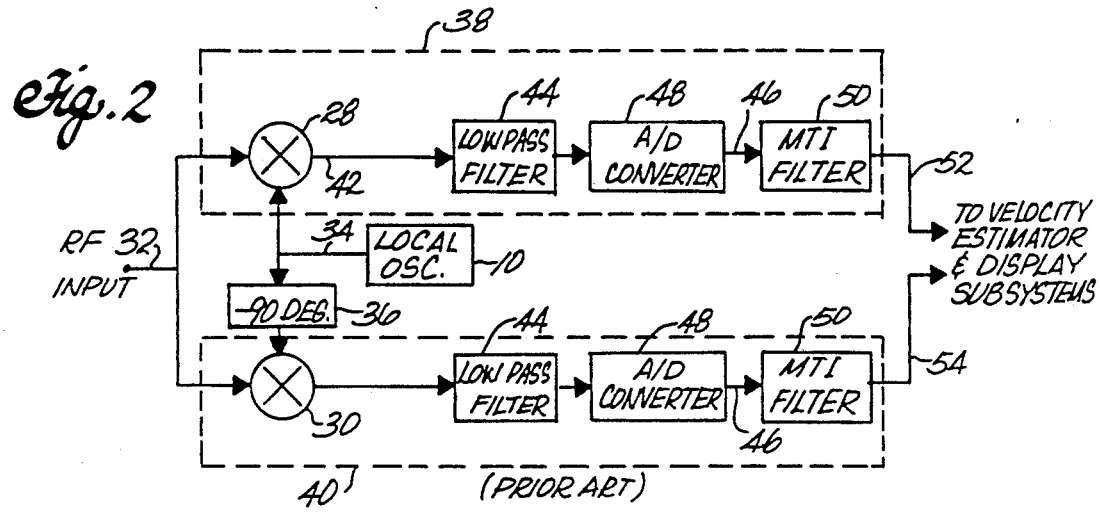
FIG. 2 is a functional block diagram illustrating a prior art Doppler signal processor for an ultrasonic imaging system.
Figure 4:
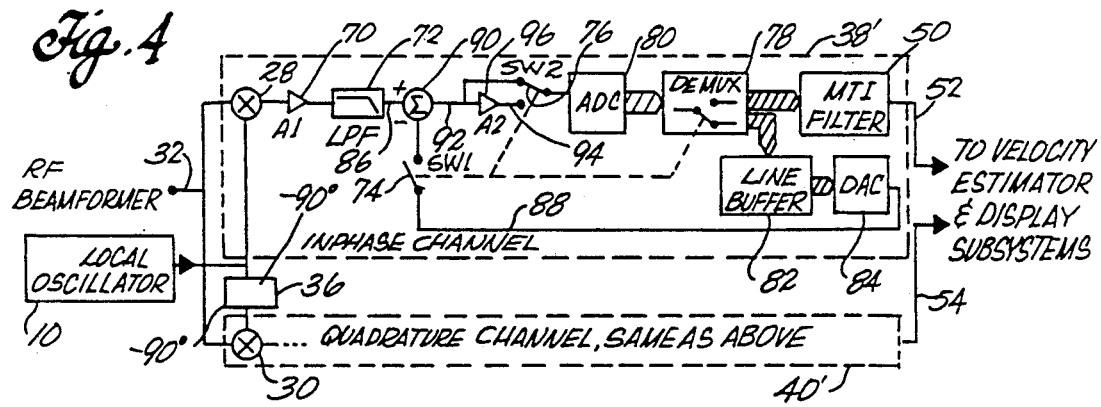
FIG. 4 is a functional block diagram of a Doppler signal processor employing a preferred embodiment of a stationary bias signal canceller system according to principles of this invention.
Figure 5:
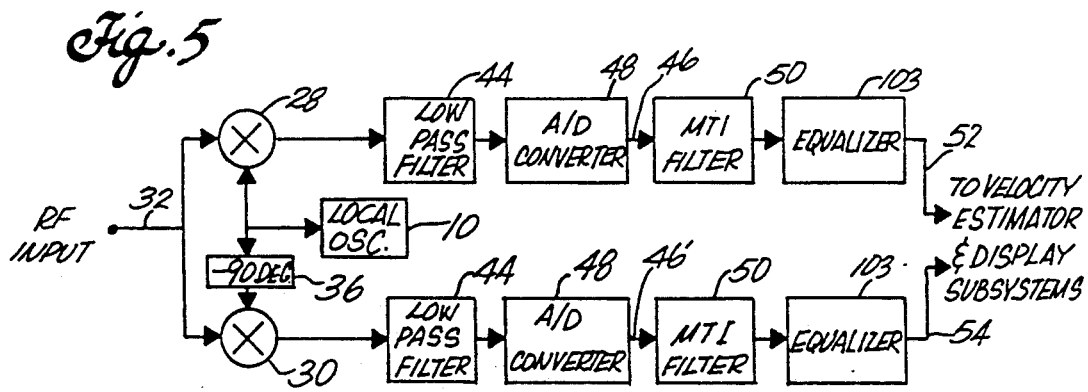
FIG. 5 is a functional block diagram illustrating an MTI filter equalization network used in conjunction with the processor of FIG. 2 according to the principles of this invention.
Figure 13:
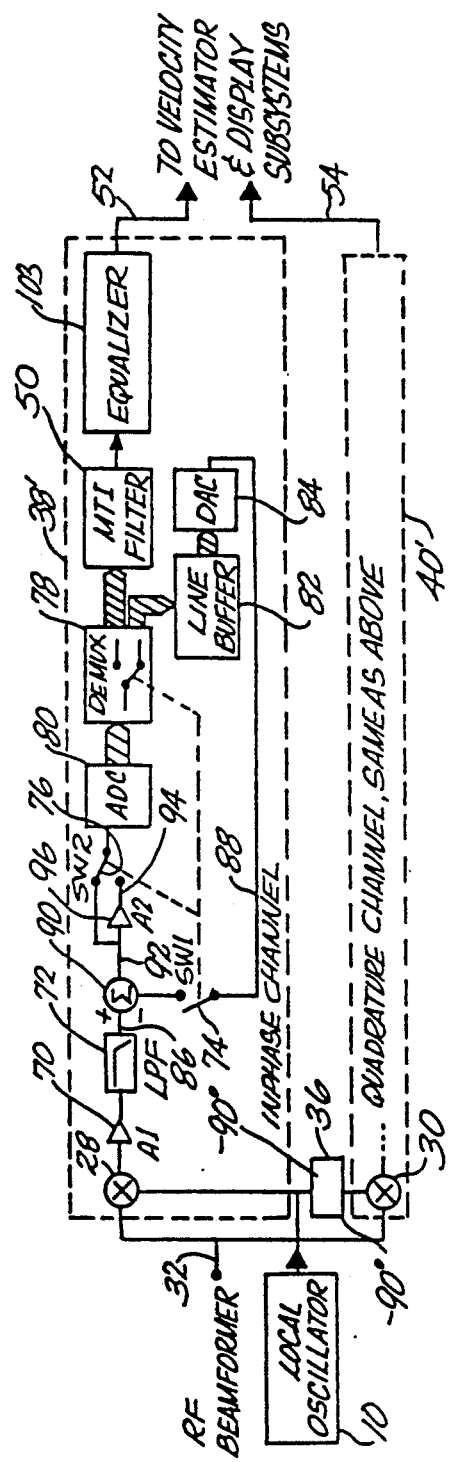
FIG. 13 is a functional block diagram illustrating the MTI filter equalization network of FIG. 10 used in conjunction with the processor of FIG. 4 according to the principles of this invention.

Referring to the drawings, FIGS. 1 and 3 illustrate conventional components of a blood flow measuring and imaging system. FIG. 2 illustrates components of a prior art Doppler signal processor for ultrasonic flow imaging. FIG. 1 is an example of one means for producing input signals to the FIG. 2 system, and FIG. 3 illustrates one type of velocity estimator and display subsystem for processing and displaying output signals from the prior art system of FIG. 2. As described below, FIGS. 4, 5 and 13 illustrate components of Doppler signal processors for ultrasonic flow imaging according to principles of this invention. The processors of FIGS. 4, 5 and 13 can also be used in conjunction with the input signals derived from the system of FIG. 1, and with the velocity estimator and display subsystem shown in FIG. 3.

Referring now to FIG. 1, a blood flow measuring system includes an oscillator 10 which generates a stable high frequency oscillation signal applied to a frequency-dividing and synchronizing circuit 12. In response to the high frequency oscillation signal, the circuit 12 generates a digital pulse signal 14 for ultrasonic pulse beam transmission. In response to the digital pulse signal 14, a driver circuit 16 applies an analog pulse signal 18 to a probe 20 through a transmit-receive changeover circuit 22. The probe 20 is excited to transmit an ultrasonic pulse beam toward a blood vessel 24 in a sector 26 of a living body under examination.

The probe 20 may be a curved linear array of the type disclosed in Plesset et al. U.S. Pat. No. 4,409,982. The beam of the probe 20 repeatedly steps through successive angles that scan the entire sector 26. During each such scan of the entire sector, the data to display one frame is acquired. Each angle at which the beam points corresponds to one "color flow line" of the sector display. At each angle, a plurality of n pulses, where n is typically between 4 and 16, are transmitted from the probe 20 and the echoes are received and Doppler processed. One "acoustic line" of data is acquired for each pulse transmission. (The value of n, i.e., the number of acoustic lines in a flow line, is selected by the equipment operator, depending upon the desired resolution and frame rate—the larger n, the lower the frame rate and the higher the velocity resolution.)

From n acoustic lines of data, one color flow line is derived. The beam then steps to the next angle in succession and n pulses are again transmitted from the probe 20 and the echoes are received and Doppler processed to derive another flow line. During Doppler processing, each transmitted pulse is sampled a relatively large number of times, e.g. up to 256 times, at successive time intervals after pulse transmission to define sample cells along the direction of the beam. The number and location of the sample cells relative to the probe 20 are selected by the equipment operator to permit diagnosis of the desired region of interest. The velocity in the region along the beam direction corresponding to each of the selected cells is calculated from the samples for that cell derived from the echoes from the n transmitted pulses.

The signal reflected from the blood vessel 24 is converted by the probe 20 into an electrical signal, and this signal is applied, through the transmit-receive changeover circuit 22, to a high frequency amplifier and beamformer 23 that focuses the reflected signal. The amplified output signal is applied to quadrature detectors (balanced mixers) 28 and 30 in the ultrasound signal processing systems illustrated in FIG. 2. The signals derived from the transducer and input to the quadrature channels at 32 may be RF or IF; use of an RF beamformer signal is a preferred embodiment. The beamformer could comprise the beamformer disclosed in application Ser. No. 07/415,404, filed Sep. 29, 1989, the disclosure of which is incorporated fully herein by reference. The described Doppler processing circuitry could be connected in parallel with the video processor of the referenced application in the diagram of its FIG. 1.

The oscillator 10 generates and applies a stable high frequency signal to the synchronizing circuit 12 which generates various output signals having a desired frequency. These output signals include a signal for causing repeated transmission of an ultrasonic pulse beam. This signal is applied through the changeover circuit 22 to the ultrasound probe 20, and the piezoelectric elements contained in the probe are excited to transmit an ultrasonic pulse beam toward and into the internal moving part of the living body under diagnosis. The internal moving part is, in this example, blood flow in the blood vessel 24. The sector 26 designates a region of scanning for the measurement of a Doppler blood flow image. A transmitter control circuit controls the ultrasonic pulse beam to transmit it at predetermined scanning angles, direction and depth toward and into the sector 26. Pulses of the transmitted ultrasonic beam reflected from the various tissue interfaces in the body sector are received by the ultrasonic probe. The received echo signal 32, after being amplified and focused by the RF amplifier and beamformer 23, is then sent to the processing systems of FIG. 2 for further processing.

In order to estimate the Doppler shifts of the echoes received from blood cells, an ultrasound imaging system must transmit several (e.g. from 4 to 16) pulses at one angle and then detect the variations in the phase of the echoes from pulse to pulse at different depths. The echoes from these pulses are range gated to define the same number of cells at different depths from the probe. The frequency shift of each range gated echo represents the velocity in the corresponding cell. Part of the conventional receiving process is shown in FIG. 2.

A quadrature baseband detection process is used in which, in this example, the RF input signal 32 from the beamformer 23 of FIG. 1 is applied to the mixers 28 and 30. Separately, the reference signal 34 from the oscillator 10 is applied to the mixers, with the reference signal sent to one mixer 30 having its phase shifted 90° by a phase shift circuit 36, so that a 90° phase-shifted reference signal is applied to the mixer 30, together with the amplified echo signal 32 from the beamformer. The reference signal 34 applied to the mixer 28, in the description to follow, is processed as part of an in-phase channel 38; and the phase-shifted signal is processed in a separate quadrature channel 40 having system components similar to the in-phase channel. Therefore, the description to follow will suffice for both channels.

The outputs of the balanced mixers 28 and 30 are analog signals representing the product of the input echo signal 32 and the input reference signal 34. The analog signal 42 is then amplified by a first amplifier, passed through a low-pass filter 44, and then amplified by a second amplifier. In the illustrated embodiment, the RF signal from the receiving beamformer is down-converted to a baseband frequency in the quadrature channels, using the balanced mixers. A swept gain function was previously applied to the RF signal to compensate for ultrasound attenuation in tissue. The first amplifier is a fixed gain stage. The low-pass filter 44 sets the detection bandwidth which can be between about 100 KHz and about 2.5 MHz.

The output signal from the second amplifier is then converted to a digital output signal 46 in an analog-to-digital converter 48 for processing in an MTI filter or stationary canceller 50 to cancel stationary components of the received echo signals. Echoes from stationary, or nearly stationary structures in the body are much stronger than the echoes from blood cells, often by as much as 60 dB. The analog-to-digital converter 48 has a large dynamic range in order to keep the blood flow signals well above quantization noise and yet not saturate on the stationary signals. The MTI filter 50 is used to remove stationary, or slowly moving components after the signal has been converted to digital by the analog-to-digital converter 48. The filter can have a comb response with notches at the pulse repetition frequency and its harmonics. The MTI filter output signals 52 and 54 from the quadrature channels can be processed by the system of FIG. 3 to extract the Doppler frequency information, at discrete ranges, either by an autocorrelation technique, or by a frequency domain processing system, such as by fast Fourier transform (FFT) techniques.

FIG. 3 illustrates components of a conventional system for further processing and imaging of the Doppler ultrasound blood flow information derived from the system shown in FIG. 2. The baseband information 52 and 54 is digitally processed in a velocity estimator 56 and a digital scan converter 58 and is then sent to a color processor 60 for further digital processing of the information. The results are converted by a digital-to-analog converter 6 into analog signals representing the three primary colors, red, green and blue, which are displayed on the CRT of a color TV monitor 64. The output signals also can be converted into standard TV signals via an encoder 66 for connection to peripheral equipment such as a VCR 68.

The embodiment of FIG. 4 illustrates an analog feedback stationary bias signal canceller for ultrasonic flow imaging according to principles of this invention. The RF signal 32 from the receiving beamformer 23 is downconverted to baseband in the quadrature channels 38' and 40', and a first amplifier 70 and low-pass filter 72 amplify the output signals and set the detection bandwidth which also may be between about 100 KHz and about 2.5 MHz. The stationary bias signal canceller operates in two modes: bias signal acquisition and then Doppler signal acquisition. These two modes occur in succession during each flow line data acquisition interval.

Electronic switches 74 and 76 and a demultiplexer 78 are shown in FIG. 4 in the bias signal acquisition mode. An analog-to-digital converter 80, the addresses of a line buffer 82, and a digital-to-analog converter 84 are all clocked at a sample rate determined by the desired resolution of a flow line. This sample rate is typically between about 200 KHz and about 5 MHz. As stated above, in each flow line measuring sequence, a number of ultrasound pulses are directed at a predetermined angle in the body sector 26 under diagnosis. One acoustic line of data is acquired for each pulse transmission.

In the bias signal acquisition mode, a single acoustic line (pulse-echo) is first transmitted and received. The resultant signal is then stored as a stationary bias signal in the line buffer 82, after which the system switches to the Doppler acquisition mode. The stored bias signal can be thought of as representing primarily stationary targets. The acoustic line that was used to acquire the stationary bias signal is not used for flow estimation. On each of the succeeding n pulses which are transmitted along the same angle and toward the same target as part of the flow line, the stored bias signal is recalled from the line buffer 82, converted to analog form by a digital-to-analog converter 84, and subtracted from the incoming signals 86 derived from the echoes from these n succeeding pulses.

During the Doppler acquisition mode, the switch 74 is closed so that the analog signal 88 from the converter 84, representing the stationary bias signal component, is fed back to a summing junction 90 for subtracting this bias signal from the subsequent signals 86. An analog residue signal 92 output from the summing junction 90 contains the pulse-to-pulse variations which principally constitute the Doppler signal. During the Doppler acquisition mode, the switch 76 is closed so that the residue signals 94, which have then been boosted in gain by the second amplifier 96, are then converted to digital in the analog-to-digital converter 80, selected by the demultiplexer 78, and processed by MTI filter 50.

A modulo n+1 counter (not shown) controls the state of switches 74 and 76 and demultiplexer 78. The counter advances one state responsive to sync circuit 12 each time a pulse is transmitted by the probe 20. After each series of n+1 pulses, the counter recycles. Thus the counter recycles each time a new flow line is generated. When the counter recycles, the bias signal acquisition mode is established, i.e. switches 74 and 76 and demultiplexer 78 are in the state shown in FIG. 4. When the counter advances to the first state, the Doppler acquisition mode is established, i.e. switches 74 and 76 and demultiplexer 78 change state.

By removing the stationary bias from the incoming signals, the circuit gain for processing the resulting Doppler signal 94 may, in general, be boosted substantially by amplifier 96 without overloading the converter 80. This increase in gain results in an improved Doppler signal-to-clutter ratio as a result of the large amplitude Doppler signal, and an increase in the dynamic range of the converter 80, the output signal of which is then used in the following process of forming the velocity estimate.

The residue signal 94 contains the pulse-to-pulse variations which constitute the Doppler signal as well as some undesired components. Signals from completely stationary tissue are removed as a result of subtraction of the bias signal, while subsequent processing by the MTI filter 50 removes the slowly varying component of the clutter. The outputs 52, 54 from the MTI filters are provided as input signals to the velocity estimator 56 of FIG. 3.

Velocity signal errors can occur in a situation where there is a strong Doppler return but no stationary echo. In this instance, the worst case error amplitude is equal to the peak Doppler signal amplitude. This error would appear as a steady-state component in the 4-to-16 sample sequence, and is also removable by the conventional type of MTI filter 50 which follows the analog-to-digital converter 80. The errors limit the amount of gain that the amplifier 96 may have and, thus, limit the improvement in Doppler signal-to-clutter ratio. In the preferred embodiment, this gain can be altered as desired to suit different pulse frequencies, operating frequencies, and the like. The circuit can also be disabled by the user if the small reduction in image frame rate is undesirable and the Doppler-to-clutter ratio is not too unfavorable in the region of interest.

In a prior art system which has used an analog feedback path around an analog-to-digital converter as part of a stationary canceller, the canceller is a first-order recursive filter which has notches at the pulse repetition frequency and its harmonics. This canceller updates its estimate of the stationary signal component on every pulse. The technique according to the present invention is different, in that it uses a single "snapshot" of data from a pulse-echo sequence to subtract a stationary bias signal from each of the succeeding 4-to-16 pulse-echo sequences that are acquired to estimate flow along one flow line. In flow imaging, only a few pulse-echo sequences are used to form estimates of the Doppler signals along each line. This invention takes advantage of the fact that, during the brief time interval used for the 4 to 16 pulses (a few milliseconds at the most), the quasi-stationary echoes from slowly moving tissue are in fact reasonably stable. Thus, the one-line sample of those echoes suffices to mostly cancel the "stationary" bias component. As a result, the system of this invention produces a higher ratio of Doppler signal-to-quantization noise with more accurate image information. The system also permits use of less expensive analog-to-digital converters with only a minimal decrease in image frame rate.

A purpose of an MTI filter is to provide a means by which stationary objects (zero velocity) are totally attenuated (cancelled) and the remaining information (non-zero velocities) are unattenuated. One problem associated with an MTI filter is in terms of its nonideal characteristics. A characteristic which can be detrimental in measuring slow flows is the frequency response of the MTI filter. The block diagram of FIG. 6 schematically shows the construction of an MTI filter such as the filter 50. An input signal x(n) is applied to an accumulator 100 and a delay stage 102 simultaneously. At some time interval ($\tau$) later, the sample previously input to the delay stage 102 becomes x(n−$\tau$) which is an exact replica of the original input, x(n), delayed in time by ($\tau$) seconds. Tau is the reciprocal of the pulse repetition frequency of the pulsed Doppler system. The output of the MTI filter is produced by subtracting the previous sample (taken $\tau$ seconds ago) from the present input sample as shown in FIG. 6.

The output of the MTI filter 50 shown in FIG. 6 may be mathematically expressed as $$y(n) = x(n) - x(n-\tau) \quad (1)$$

To evaluate the frequency response of this filter, one first performs a Z transformation on equation (1). This is shown in equations (2) and (3):

$$Z\{y(n)\} = Z\{x(n) - x(n-\tau)\} \quad (2)$$
$$= Z\{x(n)\} - Z\{x(n-\tau)\}$$

$$Y(z) = X(z) - z^{-\tau} X(z) \quad (3)$$
$$= X(z)(1 - z^{-\tau})$$

The z's in equation (3) are actually a frequency index of the form $z = \omega^{j\omega t}$. The $z^{-\tau}$ term in equation (3) represents a delay operator with a delay of $\tau$ seconds. The impulse response of the filter is defined as H(z) and is given in equation (4):

$$H(z) = \frac{Y(z)}{X(z)} = 1 - z^{-\tau} \quad (4)$$

Figure 7:
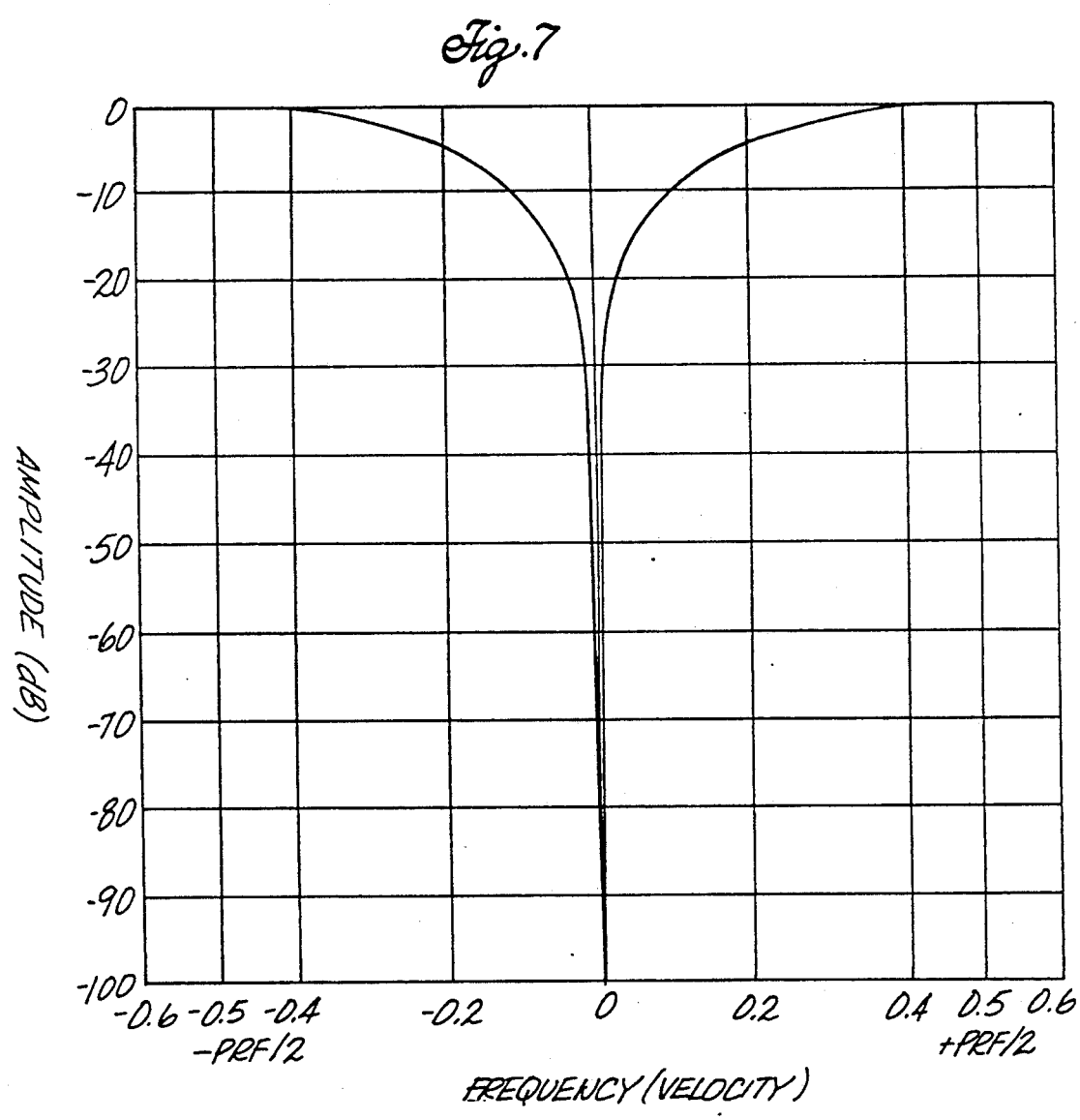
FIG. 7 is a frequency response plot of the MTI filter of FIG. 6, showing the response for positive and negative flow velocities.
Figure 9:
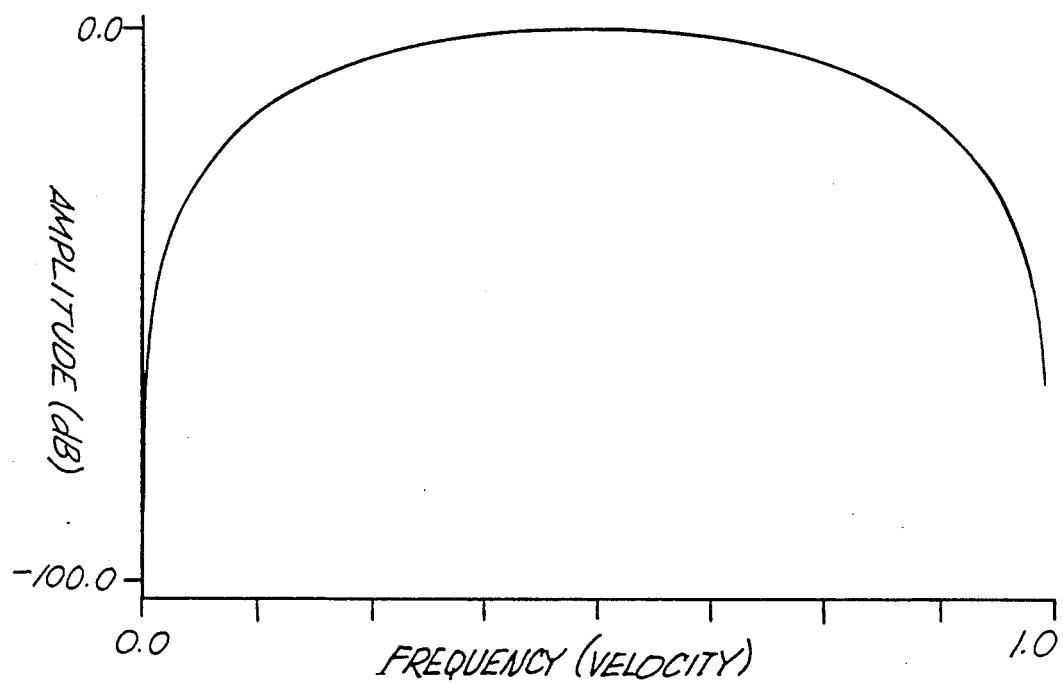
FIG. 9 is another frequency response plot of the MTI filter shown in FIG. 6, showing in detail the response for a range of positive flow velocities.

The frequency response of the MTI filter defined in equation (4) can be plotted by sweeping the frequency variable z as defined above. The frequency response is plotted in FIG. 7 where the vertical axis represents output signal amplitude and the horizontal axis represents frequency in terms of the system pulse repetition frequency (PRF), and has been normalized so that zero corresponds to the baseband frequency and to zero flow velocity. FIG. 9 is another plot of the frequency response of the MTI filter, showing the response over a greater range of positive values of normalized frequency and flow velocity. It can be seen from these plots that a null in the frequency response occurs at zero velocity. It is also apparent from this plot that flows which produce velocities close to zero are also severely attenuated. This attenuated range of flow velocities includes the range of interest for measuring blood flow, and hence produces errors in velocity estimation.

If this frequency response can be altered to produce a flatter gain across the frequency spectrum of interest prior to providing signals for velocity estimation, the velocity estimator can produce an estimate which is not biased, and hence is more accurate. In general, velocity estimator circuits are designed to operate with signals having a frequency characteristic which, ideally, is essentially flat, approaching that of white noise. Any deviation from that ideal may result in velocity errors.

Ideally, an MTI filter having a perfectly flat spectral response with a single null at zero would be desirable. Although this is not possible, in the present invention, a mechanization is provided where the MTI filter is connected to an equalizer. The combination filter/equalizer operates such that the stationary (zero velocity) portion of the input signal is first cancelled, and the remaining spectrum is then flattened (in a noise sense, it is whitened); and a very close approximation to the ideal is made.

The equalizer, which may be thought of as a spectral whitening filter, is derived from the inverse response of the MTI filter. The equalizer transfer function then becomes that given in equation (5):

$$W(z) = \frac{1}{H(z)} = \frac{1}{1 - z^{-\tau}} \quad (5)$$

The Z-transform pole zero plots of the transfer functions of H(z) and W(z) are shown in FIG. 8. The zero of the response of H(z) is shown as a circle and the pole of the response of W(z) is shown as an x. It is seen that the pole and zero cancel one another and the resultant frequency response is flat. The difficulty here is the pole location. A pole on the unit circle represents an unstable system and, therefore, should be avoided. The MTI filter does not perfectly cancel the stationary signal, and when its output signal is applied to the filter equalizer, peaking at the pole location occurs in the frequency response.

This problem is remedied by using a slightly modified transfer function for the equalizer, W(z), and the new transfer function is given in equation (6):

$$W_m(z) = \frac{1}{1 - bz^{-\tau}} \quad (6)$$

The subscript, m, in equation (6) signifies the modified equalizer and the variable b has the effect of varying the pole position of the equalizer, thereby allowing the extent to which the MTI filter is equalized to be variable, depending upon the clinical application. The range of values for b are $0 < b < 1$.

The difference equation for equation (6) can be obtained by taking the inverse Z transformation of $W_m(z)$, yielding the difference equation given in equation (7):

$$y(n) = x(n) + by(n - \tau) \quad (7)$$

Figure 10:
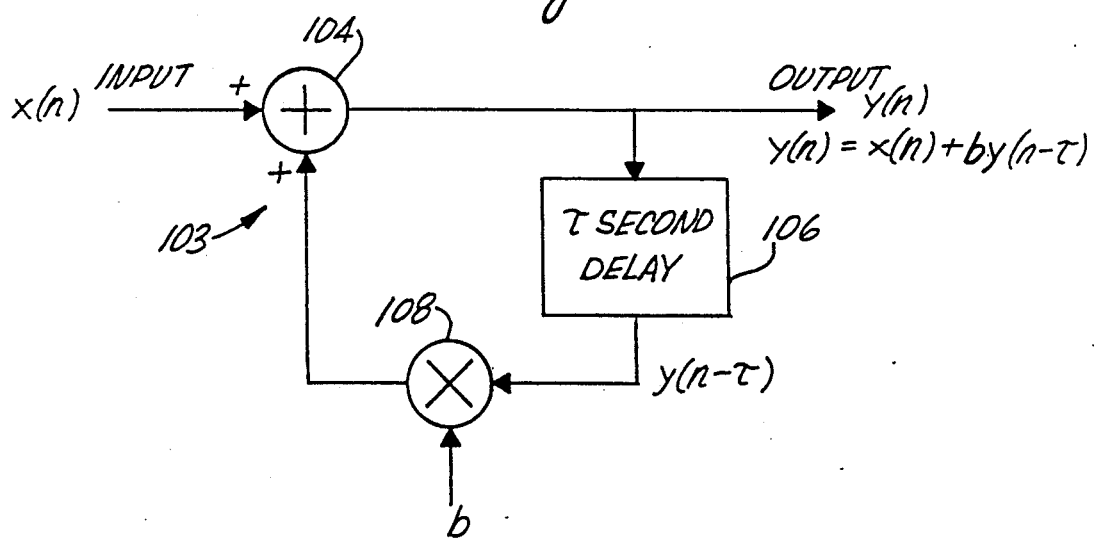
FIG. 10 is a functional block diagram of an equalization filter constructed in accordance with the teachings of the invention.

Equation (7) can be implemented using an equalizer having the structure shown in FIG. 10. The input signal x(n) is applied to one input of an accumulator 104. The output of the accumulator 104 is provided to the input of a delay stage similar in function to the delay stage 102 of FIG. 6. The output of the delay stage 106 is multiplied by variable b using multiplier 108. The output of multiplier 108 is added to the input signal x(n) by accumulator 104. The output signal from the accumulator 104 provides the output signal for the equalizer 103.

Figure 11:
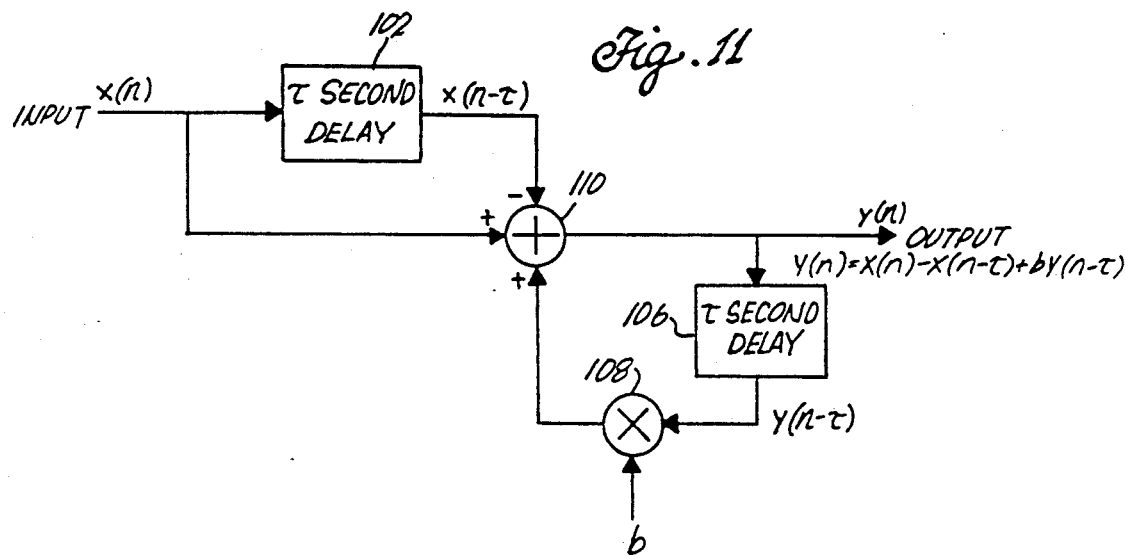
FIG. 11 is the resultant functional diagram of a prior art MTI filter combined with the equalization filter of this invention.

The hardware structures for the MTI filter 50 (FIG. 6) and the filter equalizer 103 (FIG. 10) may be combined by connecting the output from the MTI filter to the input of the equalizer. This combination is shown in FIG. 11, where the functions of the accumulators 100 and 104 are combined into a single accumulator 110 to minimize hardware.

The difference equation of the output of the combined network is given in equation (8) and is formed by summing each individual term at the summing junction of 110.

$$y(n) = x(n) - x(n-\tau) + by(n-\tau) \qquad (8)$$

The z domain equivalent of the difference equation of (8) can be found by performing the forward z transformation. The combined response ($H_{combined}$) can then be written as $$H_{combined}(z) = \frac{1 - z^{-\tau}}{1 - bz^{-\tau}} \qquad (9)$$

Figure 12:
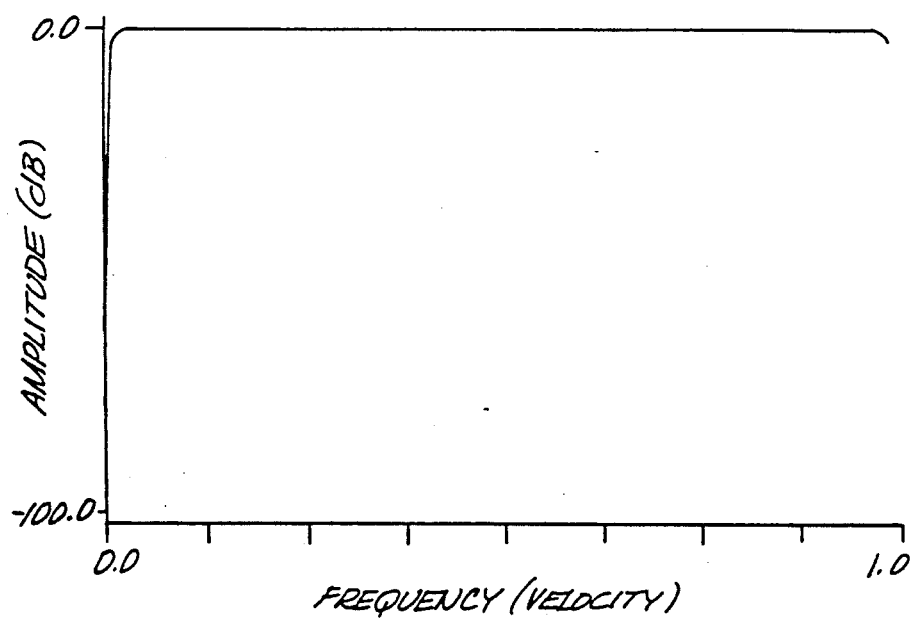
FIG. 12 is the resultant frequency response of the MTI filter and equalizer combination of this invention, depicting the flat spectrum over most of the frequency range and the sharp null centered at zero corresponding to the stationary component of the returned echo.

The combined frequency response of the MTI filter and equalizer of FIG. 11 in accordance with the principles of this invention is shown in FIG. 12. It can be seen from comparing FIGS. 9 and 12 that the equalizer 103 flattens the spectral response of the MTI filter 50 and thereby allows a velocity estimator to make an unbiased estimate. The resultant spectral response of the combined functions maintains a notch at zero velocity, which is representative of a stationary object.

FIG. 5 shows the addition of the equalizer 103 to the prior art Doppler signal processor circuit of FIG. 2. For both the in-phase and quadrature channels 38, 40, an equalizer 103 is connected between the output of the MTI filter 50 and the corresponding input 52, 54 to the velocity estimator 56 of FIG. 3.

FIG. 13 shows the addition of the equalizer 103 to the Doppler signal processor circuit of FIG. 4, which also incorporates the stationary bias signal canceller described above. For both the in-phase and quadrature channels 38', 40', an equalizer 103 is connected between the output of the MTI filter 50 and the corresponding input 52, 54 to the velocity estimator 56 of FIG. 3.

For the processor circuits in both FIGS. 5 and 13, the MTI filter 50 may be combined with the equalizer 103 as shown in FIG. 11 to eliminate the need for separate accumulators. It should be noted that, of the n acoustic lines provided to the corresponding MTI filter 50 from the processing circuits in FIGS. 2 and 4 during the acquisition of a flow line, one of those acoustic lines is devoted to initializing the delay stage 102 of the MTI filter, and hence this one acoustic line is not processed by the velocity estimator 56. In similar fashion, of the n acoustic lines provided to the corresponding MTI filter 50 and equalizer 103 from the processing circuits in FIGS. 5 and 13 during the acquisition of a flow line, one of those acoustic lines is devoted to initializing the delay stage 102 of the MTI filter, and another one of those acoustic lines is devoted to initializing the delay stage 106 of the equalizer 103. Hence these two acoustic lines are not processed by the velocity estimator 56. In other words, only n−2 acoustic lines are actually processed by the velocity estimator 56.

As a result of the use of the equalizer of the present invention, the spectral bias which normally occurs in MTI filters is effectively eliminated. The spectrally whitened flow data can then be used by the velocity estimation subsystem without adversely biasing the estimate. The overall results of the equalization scheme allow more accurate velocity estimates regardless of the type of estimator used.

While various embodiments of the invention have been described, it is anticipated that other modifications and adaptations will occur to those skilled in the art upon consideration of this disclosure. Accordingly, the invention is limited only by the appended claims.

What is claimed is:

1. An ultrasonic Doppler flow measuring and imaging system comprising:
   (a) ultrasonic wave transmitting and receiving means for sequentially transmitting a series of at least three ultrasonic waves toward and into a living body at a selected angle over a predetermined time interval and for receiving a corresponding series of reflected echo signals, wherein each reflected echo signal in the series has a stationary component representative of reflection from essentially stationary tissue and a Doppler component representative of reflection from a moving part of the body;
   (b) means for processing the series of reflected echo signals, the signal processing means including (i) means for subtracting one of the reflected echo signals from each of the other reflected echo signals to cancel the stationary component from the reflected echo signals, leaving Doppler signals representative of the Doppler component of the reflected echo signals, and (ii) means for thereafter amplifying the Doppler signals to produce a succession of output signals representative of the Doppler components of the reflected echo signals; and
   (c) means for processing the output signals to generate therefrom Doppler flow image data signals for use in imaging the moving part of the body.

2. Apparatus according to claim 1 in which the measuring and imaging system comprises an ultrasonic Doppler blood flow measuring system.

3. Apparatus according to claim 1 in which the echo signal processing means includes means for sampling the one reflected echo signal and the other reflected echo signals a plurality of times during the time, and the subtracting means comprises means for storing the samples of the one signal and subtracting the stored samples from the samples of the other signals as the latter are returned.

4. Apparatus according to claim 1 in which the echo signal processing means produces one fewer output signal than the series of ultrasonic pulses.

5. Apparatus according to claim 4 in which the echo signal processing means includes an analog-to-digital converter (ADC) to which the reflected echo signals are applied such that the ADC samples both the one signal and the other signal, an MTI filter connected to the ADC to filter the other signals, a digital register connected to the ADC to store the one signal, and a digital-to-analog converter (DAC) connected to the register to convert the stored one signal to analog form for subtraction from the other signals.

6. Apparatus according to claim 5 in which the output signal processing means includes a velocity estimator and display system connected to the MTI filter.

7. An ultrasonic Doppler flow measuring and imaging system comprising:
   (a) ultrasonic wave transmitting and receiving means for sequentially transmitting a series of ultrasonic pulses toward and into a living body at a selected angle over a predetermined time interval and for receiving a corresponding series of reflected echo signals, wherein each received echo signal has a stationary component representative of reflection from essentially stationary tissue and a Doppler component representative of reflection from a moving part of the body;

(b) means for processing the echo signals received during successive predetermined time intervals, the signal processing means including (i) an MTI filter for subtracting a stationary component from the received echo signals to thereby extract from the echo signals a Doppler signal representative of a Doppler component of the received echo signals, and (ii) equalization means having a frequency response which is substantially the inverse of the MTI filter and which is responsive to the output of the MTI filter for processing said output to produce an essentially flat frequency response over the range of frequencies being measured; and (c) means for processing the output signals from the equalizer means to generate therefrom Doppler flow image data signals for use in imaging the moving part of the body.

8. Apparatus according to claim 7 in which the measuring and imaging system comprises an ultrasonic Doppler blood flow measuring system.

9. Apparatus according to claim 7 in which the echo signal processing means includes means for sampling multiple reflected echo signals during each time interval and means for subtracting therefrom a stationary bias signal component based on fewer sampled echo signals than are present in the series of echo signals.

10. Apparatus according to claim 9 including, for each time interval, means for storing a reflected echo signal, means for sampling a plurality of other reflected echo signals, and means for subtracting the stored reflected echo signal from the sampled other echo signals to extract said Doppler signal.

11. Apparatus according to claim 10 in which the echo signal processing means includes means for passing the amplified Doppler signals through an analog-to-digital converter and means for filtering the digital output in an MTI filter.

12. Apparatus according to claim 11 in which the filter output is received by a velocity estimator and display system.

13. Apparatus according to claim 12 in which the system comprises an ultrasonic Doppler blood flow measuring system and display.

14. Apparatus according to claim 13 in which the imaging system includes color imaging.

15. Apparatus according to claim 7 in which the MTI filter has a transfer function which is $$y(n) = x(n) - x(n-\tau)$$

and the equalization means has a transfer function which is $$y(n) = x(n) + by(n-\tau)$$

where b is a variable having a value greater than zero and less than 1.

16. Apparatus according to claim 7 in which the MTI filter in combination with the equalization means has a transfer function which is $$y(n) = x(n) - x(n-\tau) + by(n-\tau)$$

where b is a variable having a value greater than zero and less than one.

17. Doppler ultrasound apparatus comprising:
means for transmitting a plurality of at least three high frequency ultrasonic pulses into a target along the same line;
means for receiving and down converting the frequency of the echoes from the pulses to form echo signals;
means for storing the echo signal from one of the pulses;
means for subtracting the echo signals from each of the other pulses from the stored echo signal to form level corrected signals;
an analog to digital converter (ADC) to which the level corrected signals are applied; and
means for digitally processing the level corrected signals from the ADC to form signals representative of the velocity along the line.

18. The apparatus of claim 17, additionally comprising means for amplifying the level corrected signals applied to the ADC.

19. The apparatus of claim 18, in which the storing means comprises:
means for applying the echo signal from the one pulse to the ADV to form a digital level correcting signal;
means for storing the level correcting signal in a buffer;
a digital to analog converter (DAC) to which the buffer is connected; and
means for controlling the buffer and the DAC to reproduce the echo signal from the one pulse in synchronism with the echo signals from each of the other pulses.

20. The apparatus of claim 19, in which the subtracting means comprises a summing junction to which the DAC and the receiving and down converting means are connected.

21. The apparatus of claim 20, in which the amplifying means comprises an amplifier between the summing junction and ADC.

22. The apparatus of claim 21, in which the storing means additionally comprises:
a first switch for alternately connecting the summing junction and the amplifier to the ADC in first and second states, respectively;
a second switch for alternately connecting the ADC to the buffer and the processing means in first and second states, respectively;
a third switch for disconnecting and connecting the DAC to the summing junction in first and second states, respectively;
means for placing the first, second, and third switches in the first state during reception of the echoes from the one pulse; and
means for placing the first, second, and third switches in the second state during reception of the echoes from the other pulses.

23. The apparatus of claim 22, additionally comprising:
means for transmitting a plurality of at least three high frequency ultrasonic pulses along each of a plurality of different lines to insonify a cross sectional area of the target;
means for forming a velocity representative signals for each of the different lines in the manner set forth for the first named line; and
means for forming a color flow image from the velocity representative signals.

24. The apparatus of claim 17, in which the receiving and converting means also forms quadrature echo signals, the apparatus additionally comprising:
   means for storing the quadrature echo signal from the one pulse;
   means for subtracting the quadrature echo signals from each of the other pulses from the stored quadrature echo signal to form quadrature level corrected signals;
   an analog to digital converter (ADC) to which the level corrected signals are applied; and
   means for digitally processing the quadrature level corrected signals from the ADC with the first named level corrected signals to form the signals representative of the velocity along the line.

25. The apparatus of claim 17, in which the storing means comprises:
   means for applying the echo signal from the one pulse to the ADC to form a digital level correcting signal;
   means for storing the level correcting signal in a buffer;
   a digital to analog converter (DAC) to which the buffer is connected; and
   means for controlling the buffer and the DAC to reproduce the echo signal from the first pulse in synchronism with the echo signals from each of the other pulses.

26. The apparatus of claim 17, in which the processing means comprises;
   an MTI filter having a given frequency response for processing the level corrected echo signals from the ADC;
   an equalizer having a frequency response that is substantially the inverse of that of the MTI filter for processing the MTI filtered echo signals to form equalized echo signals, the MTI filter and the equalizer together having a substantially flat frequency response over the frequency range of the Doppler signal except for a notch at zero frequency; and
   means for processing the equalized signals from the ADC to form signals representative of the velocity along the line.

27. The apparatus of claim 26, additionally comprising an analog to digital converter (ADC) to which the echo signals are applied so that the MTI filter, the equalizer, and the processing means operate upon digital signals.

28. The apparatus of claim 27, in which the plurality of ultrasonic pulses comprises at least four pulses and the MTI filter comprises means for delaying the respective echo signals by a time interval equal to the interval between the ultrasonic pulses and subtracting the delayed echo signals from the respective echo signals to form MTI filtered echo signals.

29. The apparatus of claim 28, in which the equalizer comprises means for delaying the respective equalized echo signals by a time interval equal to the interval between the ultrasonic pulses and subtracting the delayed echo signals from the respective MTI filtered echo signals to form the equalized echo signals.

30. The apparatus of claim 29, in which the equalizer additionally comprises means for multiplying the delayed echo signals by an adjustable factor that is less than one.

31. The apparatus of claim 30, additionally comprising:
   means for transmitting a plurality of at least three high frequency ultrasonic pulses along each of a plurality of different lines to insonify a cross sectional area of the target;
   means for forming velocity representative signals for each of the different lines in the manner set forth for the first named line; and
   means for forming a color flow image from the velocity representative signals.

32. The apparatus of claim 26, in which the receiving and converting means also forms quadrature echo signals, the apparatus additionally comprising:
   an analog to digital converter (ADC) to which the quadrature echo signals are applied;
   an MTI filter having a given frequency response for processing the quadrature echo signals;
   an equalizer having a frequency response that is substantially the inverse of that of the MTI filter for processing the MTI filtered quadrature echo signals to form equalized quadrature echo signals, the MTI filter and the equalizer together having a substantially flat frequency response over the frequency range of the Doppler signal except for a notch at zero frequency; and
   means for processing the equalized quadrature echo signals to form signals representative of the velocity along the line.

33. The apparatus of claim 17, in which the storing means stores the echo signal from the first occurring pulse of the plurality.

34. The apparatus of claim 17, in which the transmitting means comprises an array of ultrasonic transducers and the receiving means comprises a beamformer, means for applying the echoes received by the array to the beamformer, and means for down converting the output from the beamformer to form the echo signals.

35. Doppler ultrasound apparatus comprising:
   means for transmitting a plurality of at least three high frequency ultrasonic pulses into a target along the same line at a pulse repetition frequency (PRF);
   means for receiving and down converting the frequency of the echoes from the pulses to form echo signals;
   an MTI filter having a given frequency response for processing the echo signals;
   an equalizer having a frequency response that is substantially the inverse of that of the MTI filter for processing the MTI filtered echo signals to form equalized echo signals, the MTI filter and the equalizer together having a substantially flat frequency response over the frequency range of the Doppler signal except for a notch at zero frequency; and
   means for processing the equalized echo signals to form signals representative of the velocity along the line.

36. The apparatus of claim 35, additionally comprising an analog to digital converter (ADC) to which the echo signals are applied so that the MTI filter, the equalizer, and the processing means operate upon digital signals.

37. The apparatus of claim 36, in which the MTI filter comprises means for delaying the echo signals by a time interval equal to the reciprocal of the PRF and subtracting the delayed echo signals from the respective echo signals to form MTI filtered echo signals.

38. The apparatus of claim 37, in which the equalizer comprises means for delaying the equalized echo signals by a time interval equal to the reciprocal of the PRF and subtracting the delayed echo signals from the respective MTI filtered echo signals to form the equalized echo signals.

39. The apparatus of claim 38, in which the equalizer additionally comprises means for multiplying the delayed echo signals by an adjustable factor that is less than one.

40. The apparatus of claim 39, additionally comprising:

means for transmitting a plurality of at least three high frequency ultrasonic pulses along each of a plurality of different lines to insonify a cross sectional area of the target;

means for forming velocity representative signals for each of the different lines in the manner set forth for the first named line; and means for forming a color flow image from the velocity representative signals.

* * * * *

UNITED STATES PATENT AND TRADEMARK OFFICE
CERTIFICATE OF CORRECTION

PATENT NO. : 5,188,112

DATED : February 23, 1993

INVENTOR(S) : Michael R. Sturgill; Bradley K. Herres; Paul M. Jaeger

It is certified that error appears in the above-identified patent and that said Letters Patent is hereby corrected as shown below:

```
Column 4, line 67, after "et al." insert a comma.
Column 5, line 47, before "FIG." delete "its".
Column 6, line 41, change "KHz" to -- kHz --.
Column 6, line 49, change "dB" to -- db --.
Column 7, line 4, change "6" to -- 62 --.
Column 7, line 17, change "KHz" to -- kHz --.
Column 7, line 29, change "KHz" to -- kHz --.
Column 9, line 35, change "z=ω^{jωt}" to -- z=e^{jωt} --.
Column 10, line 54, after "equalizer" insert -- 103 --.
```

In the Claims

```
Column 12, line 39, after "time" insert -- interval --.
Column 14, line 24, change "ADV" to -- ADC --.
Column 14, line 64, before "velocity" delete "a".
```

Signed and Sealed this

Eighteenth Day of January, 1994

Attest:

BRUCE LEHMAN

*Attesting Officer*     Commissioner of Patents and Trademarks